(12) United States Patent
Nanbu et al.

(10) Patent No.: US 6,561,033 B2
(45) Date of Patent: May 13, 2003

(54) LINE LENGTH MEASURING DEVICE FOR FISHING REEL

(75) Inventors: Kazuya Nanbu, Saitama (JP); Makoto Chiba, Saitama (JP)

(73) Assignee: Daiwa Seiko, Inc., Tokyo (JP)

( * ) Notice: Subject to any disclaimer, the term of this patent is extended or adjusted under 35 U.S.C. 154(b) by 0 days.

(21) Appl. No.: 09/983,474

(22) Filed: Oct. 24, 2001

(65) Prior Publication Data

US 2002/0139192 A1 Oct. 3, 2002

(51) Int. Cl.[7] .............................. G01B 5/18; G04F 3/00; A01K 89/015
(52) U.S. Cl. ..................... 73/597; 242/223; 242/319; 367/99
(58) Field of Search .................. 73/597, 598; 242/223, 242/319; 367/99

(56) References Cited

U.S. PATENT DOCUMENTS

| | | | | |
|---|---|---|---|---|
| 5,395,065 A | * | 3/1995 | Hirose | 242/223 |
| 5,427,323 A | * | 6/1995 | Kaneko et al. | 242/223 |
| 5,503,341 A | * | 4/1996 | Kaneko et al. | 242/223 |
| 5,645,237 A | * | 7/1997 | Kaneko | 242/223 |

FOREIGN PATENT DOCUMENTS

| | | | | |
|---|---|---|---|---|
| JP | 03-223614 A | | 10/1991 | |
| JP | 5-23082 | | 2/1993 | |
| JP | 0503882 A | * | 2/1993 | ......... A01K/89/015 |
| JP | 7-39284 | | 2/1995 | |
| JP | 08308448 A | * | 11/1996 | ......... A01K/89/015 |
| JP | 09096517 A | * | 4/1997 | ........... G01B/17/00 |

* cited by examiner

*Primary Examiner*—Helen Kwok
*Assistant Examiner*—Rose M. Miller
(74) *Attorney, Agent, or Firm*—Sughrue Mion, PLLC

(57) ABSTRACT

A line length measuring device for a fishing reel in which the spool diameter data is obtained on the basis of the time for which an ultrasonic wave is radiated from the ultrasonic sensor mounted on a reel main body onto a spool face of the spool and its reflected wave is received by the ultrasonic sensor, and the line length is measured from the spool diameter data and the number of rotations of the spool detected by rotational number detecting means and displayed. A velocity measuring device is provided for detecting a velocity of the ultrasonic wave radiated from the ultrasonic sensor, in which the spool diameter data is acquired on the basis of the velocity of ultrasonic wave measured by the velocity measuring means.

2 Claims, 4 Drawing Sheets

LINE LENGTH MEASURING DEVICE FOR FISHING REEL

BACKGROUND OF THE INVENTION

The present invention relates to a line length measuring device for a fishing reel employing an ultrasonic sensor.

To improve the angling, in recent years, most fishing reels are equipped with a line length measuring device as disclosed in JP-A-5-23082, in which the line length measuring device measures the amount of delivering the fishline or the amount of winding the line to allow a contrivance to be let out at a predetermined shelf position.

The line length measuring device has an ultrasonic sensor for transmission and an ultrasonic sensor for reception that are mounted on a reel main body in almost V-character shape to a spool face of a spool, in which the spool diameter data is obtained on the basis of the time for which an ultrasonic wave radiated by the ultrasonic sensor for transmission onto the spool face of the spool is received by the ultrasonic sensor for reception, the line length is measured and calculated in accordance with the spool diameter data and the number of rotations of the spool detected by rotational number detecting means, and the measured value is displayed on a display screen of an operation panel.

However, due to a property of fluctuating with the sound wave, the ultrasonic wave is affected under the service environment of the ultrasonic sensor, and the velocity of ultrasonic wave is varied along with the temperature.

Since the line length measuring device did not take into consideration the change in the velocity of ultrasonic wave due to environmental variations on the fishing spot, there was the risk that the line length could not be measured correctly even with a slight error due to a temperature change.

Thus, the present applicant has made improvements on the line length measuring device as described in JP-A-7-39284, and has proposed the line length measuring device in which an error in line length measurement due to a temperature change is resolved.

This line length measuring device has a temperature sensor for sensing the ambient temperature around the fishing reel mounted on the reel main body, and from the ambient temperature T° C. sensed by the temperature sensor, the velocity of ultrasonic wave is calculated in accordance with the following calculation expression Velocity=(331.5+0.61T)m/sec in which this calculated velocity of ultrasonic wave is used for measuring the line length. With the line length measuring device, the line length measurement is enabled at high accuracy by means of the ultrasonic sensor without being affected by the environmental variations around the fishing spot through all the seasons.

However, the line length measuring device, like that as disclosed in JP-A-5-23082, has two ultrasonic sensors for transmission and reception on the reel main body, and further requires a temperature sensor to be mounted on the reel main body, in addition to the ultrasonic sensor, so that the entire reel is increased in size and weight due to a mounting space, and the number of parts is increased, leaving the problems with a complicated structure, and higher manufacturing costs.

The present invention has been achieved in the light of the above-mentioned problems, and it is an object of the invention to provide a line length measuring device for fishing reel that can measure the line length at high accuracy by means of an ultrasonic sensor without being affected by environmental changes of the fishing spot, while reducing the entire reel in size and weight and simplifying the structure with lower costs.

SUMMARY OF THE INVENTION

In order to accomplish the above object, according to an aspect of the present invention, there is provided a line length measuring device for a fishing reel that measures and displays the line length from the spool diameter data and the number of rotations of a spool detected by rotational number detecting means by acquiring the spool diameter data on the basis of the time for which an ultrasonic wave is radiated from an ultrasonic sensor mounted on a reel main body onto a spool face of the spool and its reflected wave is received by the ultrasonic sensor, characterized by comprising velocity measuring means for detecting a velocity of ultrasonic wave radiated from the ultrasonic sensor, in which the spool diameter data is acquired on the basis of the velocity of ultrasonic wave measured by the velocity measuring means.

According to another aspect of the invention, there is provided the line length measuring device for the fishing reel, characterized in that the fishing reel comprises a single ultrasonic sensor, a spool direction reflection portion for reflecting an ultrasonic wave radiated from the ultrasonic sensor onto the spool face of the spool, and a direct reflection portion for directly reflecting the ultrasonic wave radiated from the ultrasonic sensor onto the ultrasonic sensor, wherein velocity measuring means calculates the velocity of ultrasonic wave on the basis of the time for which the ultrasonic wave is reflected from the direct reflection portion and its reflected wave is received by the ultrasonic sensor.

The line length measuring device according to one aspect of the invention obtains the line length from the spool diameter data and the number of rotations of the spool detected by rotational number detecting means by acquiring the spool diameter data on the basis of the time for which an ultrasonic wave is radiated from an ultrasonic sensor onto the spool face of the spool and its reflected wave is received by the ultrasonic sensor, in which in measuring the line length, the spool diameter data is based on the velocity of ultrasonic wave measured by velocity measuring means.

The line length measuring device according to another aspect of the invention obtains the line length from the spool diameter data and the number of rotations of the spool detected by rotational number detecting means by acquiring the spool diameter data on the basis of the time for which an ultrasonic wave is radiated from the ultrasonic sensor onto the spool face of the spool direction reflection portion and its reflected wave is received by the ultrasonic sensor, in which in measuring the line length, velocity measuring means calculates the velocity of ultrasonic wave on the basis of the time for which the ultrasonic wave is reflected from the direct reflection portion and its reflected wave is received by the ultrasonic sensor.

The present disclosure relates to the subject matter contained in Japanese patent application No. 2000-190535 (filed on Jun. 26, 2000), which is expressly incorporated herein by reference in its entirety.

DESCRIPTION OF THE PREFERRED EMBODIMENT

The preferred embodiments of the present invention will be described below with reference to the accompanying drawings.

Figure 1:
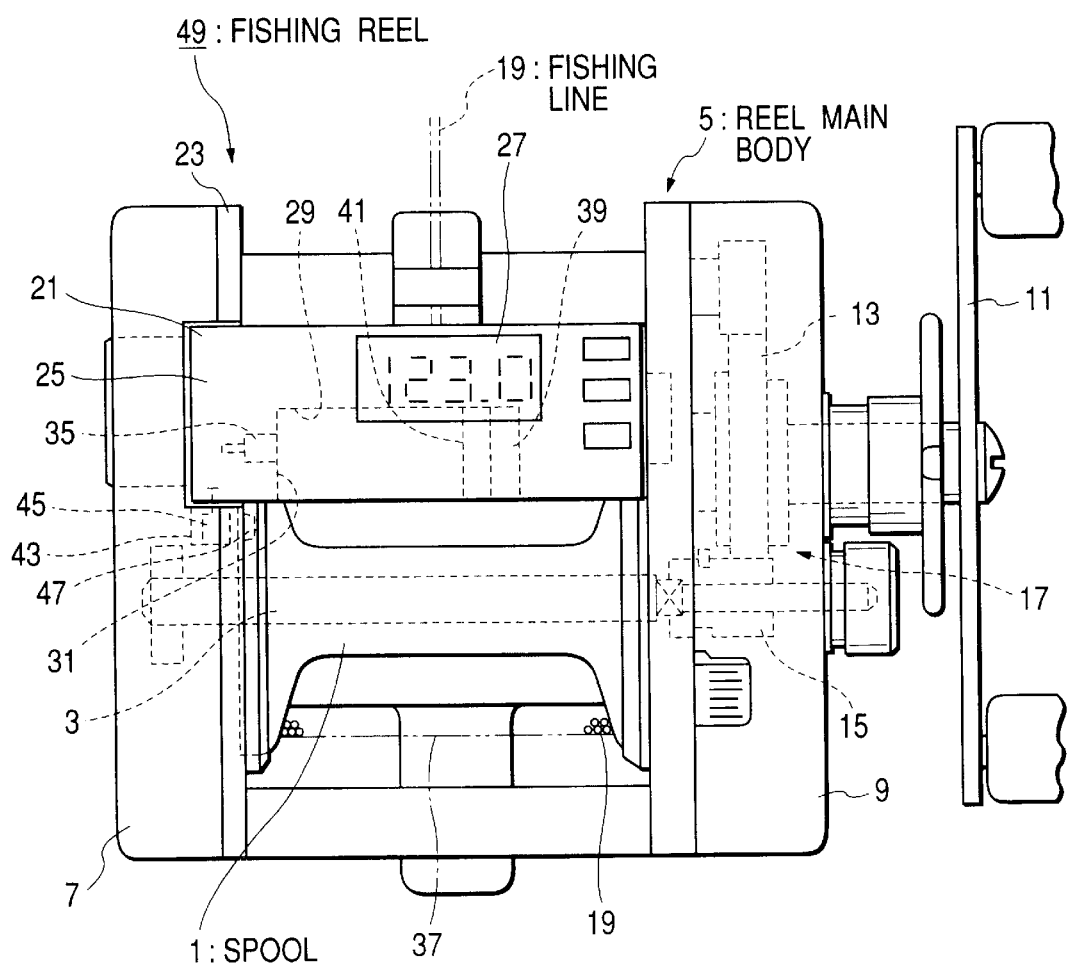
FIG. 1 is a plan view of a fishing reel having a line length measuring device according to one embodiment of the present invention.

FIG. 1 is a view showing a fishing reel having a line length measuring device according to one embodiment of the present invention as set forth in claims 1 and 2. In FIG. 1, reference numeral 1 denotes a spool supported rotatably between side plate 7, 9 of a reel main body 5 via a spool shaft 3, and reference numeral 11 denotes a handle mounted on a side plate 9, in which a rotational force of the handle 11 is transmitted to the spool 1 by a power transmission mechanism 17 consisting of a drive gear 13 and a pinion gear 15 that are attached within the side plate 9 to wind a fishline.

Also, reference numeral 21 denotes a control box placed in front of and on the upper portion of a frame 23 in the reel main body 5, in which a display 27 for displaying the line length (amount of delivery) of fishline 19 is provided on an operation panel 25 of its upper face.

Figure 2:
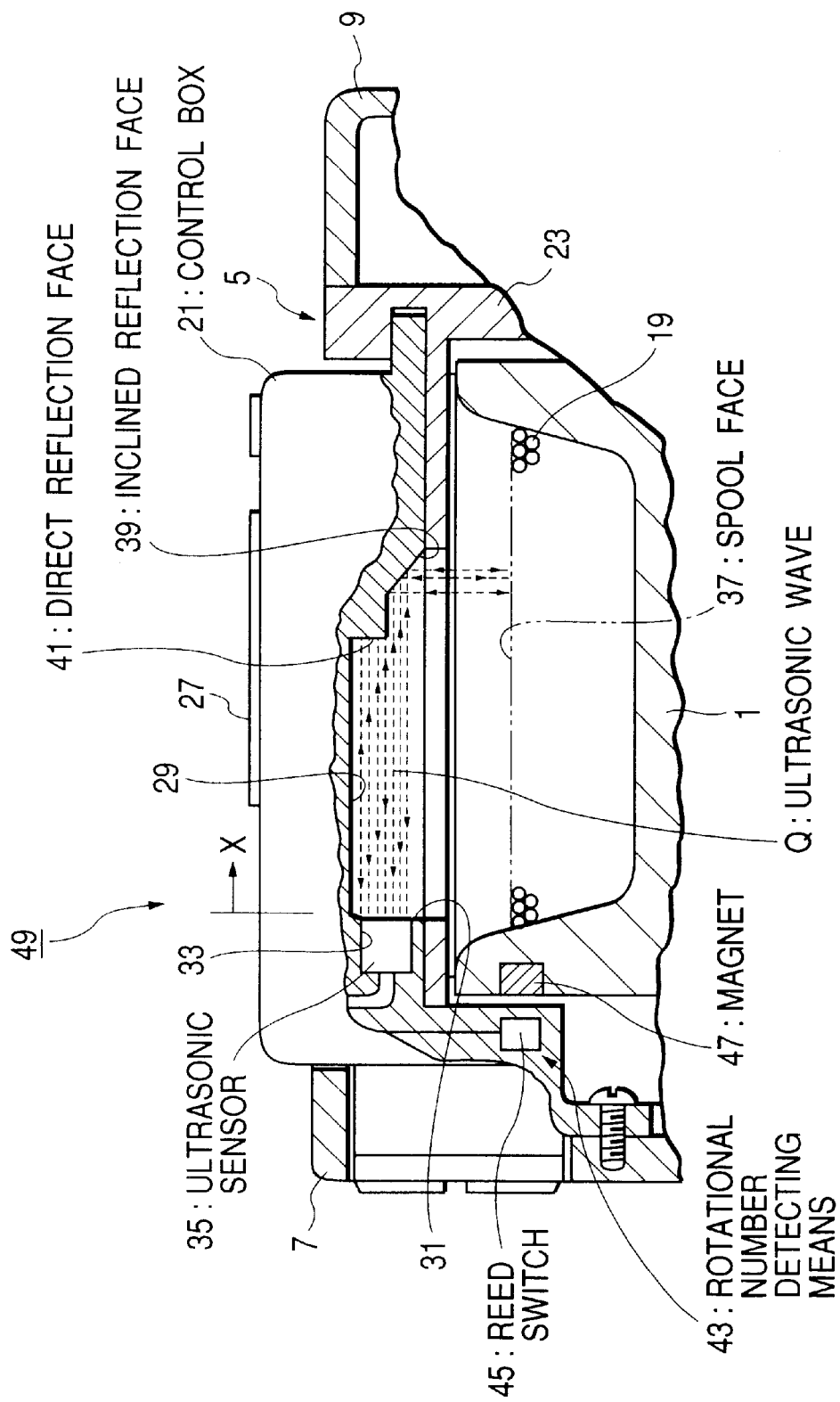
FIG. 2 is an enlarged cut-away view of the essential part of the fishing reel as shown in FIG. 1.
Figure 3:
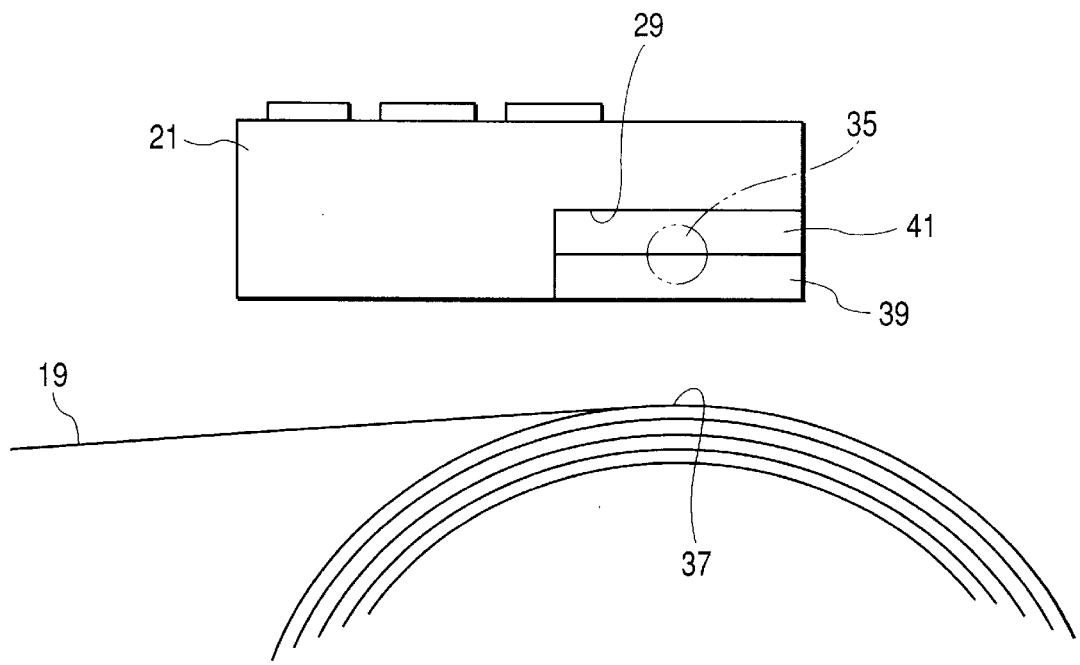
FIG. 3 is a perspective view of the fishing reel taken along the X direction in FIG. 2.

And a notch 29 is formed on the rear bottom of the control box 21 as shown in FIGS. 2 and 3, and a single ultrasonic sensor 35 for radiating an ultrasonic wave Q along the spool shaft 3 in a direction toward the side plate 9 is accommodated within a sensor mounting hole 33 provided in one side face 31 of the notch 29 on the hand of a side plate 7.

Figure 4:
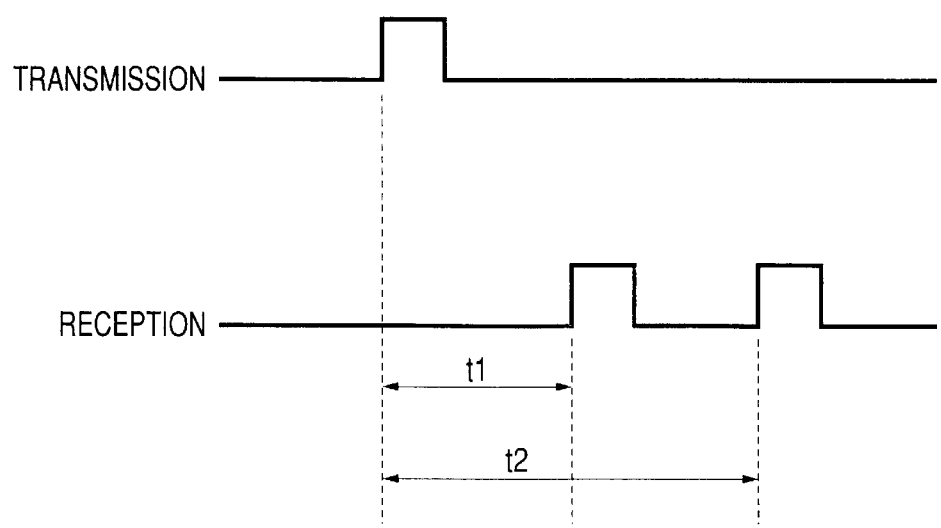
FIG. 4 is an explanatory view for explaining the transmission and reception states of ultrasonic wave with an ultrasonic sensor.

Also, the notch 29 on the hand of the side plate 9 is formed with an inclined reflection face (spool direction reflection portion) 39 for reflecting an ultrasonic wave Q radiated from the ultrasonic sensor 35 onto a spool face 37 of the spool 1, and passing its reflected wave from the spool face 37 back to the ultrasonic sensor 35, and a direct reflection face (direct reflection portion) 41 for reflecting a part of ultrasonic wave Q radiated from the ultrasonic sensor 35 directly to the ultrasonic sensor 35, which are placed vertically. As shown in FIG. 4, the time t1 for which ultrasonic wave Q radiated from the ultrasonic sensor 35 is reflected directly from the direct reflection face 41 and received by the ultrasonic sensor 35 is set to be shorter than the time t2 for which the ultrasonic wave Q is reflected from the inclined reflection face 39 and the spool face 37 and received by the ultrasonic sensor 35.

A microcomputer that builds in the line length measuring device of this embodiment and a timer are accommodated within the control box 21.

In FIG. 2, reference numeral 43 denotes rotational number detecting means for detecting the number of rotations and the rotational direction of the spool 1. The rotational number detecting means 43 comprises a pair of reed switches 45 attached to the control box 21 and a magnet 47 opposed to them and fixed a peripheral edge portion at one end of the spool 1. The line length measuring device of this embodiment calculates the spool diameter data on the basis of the time t2 for which the ultrasonic wave Q radiated from the ultrasonic sensor 35 is reflected against the inclined reflection face 39 and the spool face 37 and its reflected wave is received by the ultrasonic sensor 35. Then, the microcomputer measures the line length on the basis of the spool diameter data and the number of rotations of the spool 1 detected by the rotational number detecting means 43, and displays the measured value on the display 27. As previously described, the ultrasonic wave Q is affected under the service environment of the ultrasonic sensor 35, and the velocity of ultrasonic sensor Q is varied along with the temperature.

Figure 5:
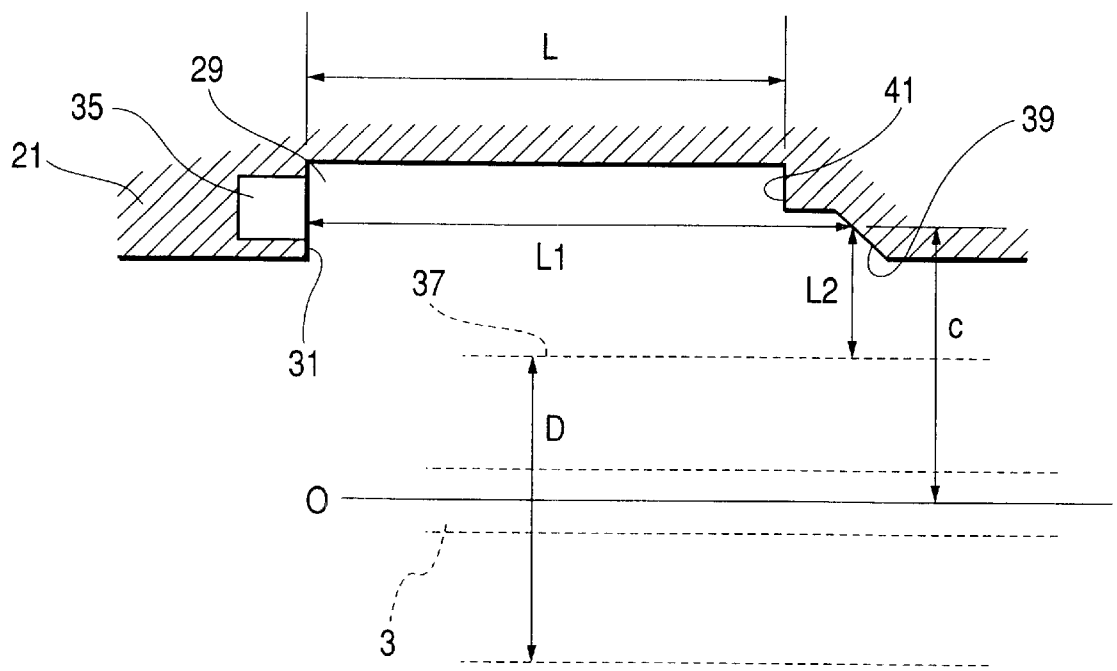
FIG. 5 is an explanatory view for explaining the measurement of line length.

A CPU of the microcomputer measures the time t1 for which the ultrasonic wave Q radiated from the ultrasonic sensor 35 is reflected against the direct reflection face 39 and received by the ultrasonic sensor 35 by the use of the timer, and calculates the velocity V(m/sec) of ultrasonic wave Q during the actual fishing on the basis of the time t1 and the distance L from the ultrasonic sensor 35 to the direct reflection face 42 as shown in FIG. 5. Then, the CPU calculates, on the basis of the velocity V(m/sec), the distance between the spool face 37 and the ultrasonic sensor 35, that is, a sum of the distance L1 between the ultrasonic sensor 35 and the inclined reflection face 39 and the distance L2 between the inclined reflection face 39 and the spool face 37, in accordance with the following calculation expression stored in a ROM of the microcomputer, $$\text{Distance } (L1+L2) = \text{velocity } V(m/sec) \times \frac{1}{2} \times \text{time } t2 \quad (1)$$

Also, the CPU calculates the spool diameter D for the fishline 19 wound around the spool 1 in accordance with the following calculation expression stored in the ROM, $$\text{Spool diameter } D = (c-L2) \times 2 \quad (2)$$

In this calculation expression (2), c is the distance between the inclined reflection face 39 and a shaft center O of the spool shaft 3. Also, the distance L2 can be easily calculated from the calculated value of the calculation expression (1) because the distance L1 is constant. And the distances L and L1 are stored beforehand in the ROM of the microcomputer.

Further, the CPU calculates the line length on the basis of the actual rotational number N of the spool 1 measured by the rotational number detecting means 43 and the spool diameter D calculated in accordance with the above expression (2) and in accordance with the following calculation expression stored in the ROM $$\text{Line length} = \pi \cdot D \cdot N \quad (3)$$

and displays the calculated result via a display drive circuit on the display 27.

With the line length measuring device of this embodiment constituted in the above manner, the CPU of the microcomputer obtains the time t1 for which the ultrasonic wave Q radiated from the ultrasonic sensor 35 is reflected from the direct reflection face 39 and received by the ultrasonic sensor 35 during the actual fishing, calculates the velocity V(m/sec) of ultrasonic wave Q during the actual fishing on the basis of the time t1 and the distance L from the ultrasonic sensor 35 to the direct reflection face 42, and calculates the line length on the basis of the velocity V(m/sec) and in accordance with the above calculation expressions (1) to (3) to display the calculated value on the display 27 of the operation panel 25. Hence, the fisher only needs to let out the fishline 19 while checking the line length displayed on the display 27.

In this way, in this embodiment, considering that the velocity of ultrasonic wave is varied along with the temperature, the velocity V (m/sec) of ultrasonic wave Q is calculated during the actual fishing and the line length is calculated and measured on the basis of the velocity V(m/sec), whereby the line length measurement is enabled at high accuracy by the use of the ultrasonic sensor 35 without employing the temperature sensor as is the case with the line length measuring device as disclosed in JP-A-7-39284.

With this embodiment, the temperature sensor is unnecessary, and the line length measurement is enabled by the use of the single ultrasonic sensor 35 mounted on the bottom of the control box 21, whereby the entire fishing reel 49 is prevented from in size and weight, and the number of parts is decreased to simplify the structure and reduce the manufacturing costs.

Though in this embodiment the invention is applied to a manual fishing reel, it is needless to say that the invention may be applied to a fishing electric reel having a spool driving motor, and further, the invention can be also applied to a fishing reel having the ultrasonic sensor 35 mounted on a thumb rest or side plate, instead of the control box 21, and a fishing reel having an ultrasonic sensor mounted on an ultrasonic sensor support as disclosed in JP-A-7-39284.

This invention is applicable to a fishing reel having the ultrasonic sensor for transmission and the ultrasonic sensor for reception in almost V-character shape with respect to the spool face of the spool, like the line length measuring device as disclosed in JP-A-7-39284, in which this fishing reel may be provided with the direct reflection portion for reflecting a part of ultrasonic wave radiated from the ultrasonic sensor for transmission directly to the spool face to the ultrasonic sensor for transmission, and the velocity of ultrasonic wave during the actual fishing can be measured by the velocity measuring means in the same manner as the above embodiment.

This fishing reel has two ultrasonic sensors for transmission and reception but does not require the temperature sensor, resulting in smaller size as the entire reel.

Further, in the embodiment, the CPU of the microcomputer the velocity V(m/sec) of ultrasonic wave Q on the basis of the time t1 for which the ultrasonic wave Q radiated from the ultrasonic sensor 35 is reflected from the direct reflection face 39 and received by the ultrasonic sensor 35 and the distance L from the ultrasonic sensor 35 to the direct reflection face 41, as described previously, but may make the line length measurement by measuring the velocity of ultrasonic wave with the temperature change in accordance with a map in which the relation between the time t1 and the velocity is stored in the ROM, whereby it is possible to accomplish the stated object with this structure, like the above embodiment.

As described above, the line length measuring device according to an aspect of the invention allows the line length to be measured at high accuracy by means of the ultrasonic sensor while, the entire reel is reduced in size and weight and the structure is simplified with lower costs without needs of mounting the temperature sensor on the reel main body.

Also, with the line length measuring device according to another aspect of the invention, the fishing reel can be reduced in size and weight by the use of the single ultrasonic sensor, and the number of parts can be decreased, whereby the structure is further simplified with the lower manufacturing costs.

What is claimed is:

1. A line length measuring device for a fishing reel that measures and displays the line length from the spool diameter data and the number of rotations of a spool detected by rotational number detecting means by acquiring the spool diameter data on the basis of the time for which an ultrasonic wave is radiated from an ultrasonic sensor mounted on a reel main body onto a spool face of said spool and its reflected wave is received by said ultrasonic sensor, comprising:

velocity measuring means for detecting a velocity of ultrasonic wave radiated from said ultrasonic sensor, in which said spool diameter data is acquired on the basis of said velocity of ultrasonic wave measured by said velocity measuring means, wherein said fishing reel comprises a single ultrasonic sensor, a spool direction reflection portion for reflecting an ultrasonic wave radiated from said ultrasonic sensor onto said spool face of said spool, and a direct reflection portion for directly reflecting the ultrasonic wave radiated from said ultrasonic sensor onto said ultrasonic sensor, wherein velocity measuring means calculates the velocity of ultrasonic wave on the basis of the time for which the ultrasonic wave is reflected from said direct reflection portion and its reflected wave is received by the ultrasonic sensor.

2. A line length measuring device for a fishing reel in which a fishline is wound onto or delivered from a spool outer face, said device comprising:

an ultrasonic sensor; and a reflector having first and second reflecting surfaces, for reflecting ultrasonic waves emitted by the ultrasonic sensor in order to measure the line length of the fishline of the fishing reel, wherein:

said first surface is oriented to have 90 degrees with respect to an ultrasonic wave emitted from the ultrasonic sensor; and said second surface is oriented to have 45 degrees with respect to the ultrasonic wave emitted from the ultrasonic sensor.

* * * * *